United States Patent [19]

Yasutake

[11] Patent Number: 5,324,935
[45] Date of Patent: Jun. 28, 1994

[54] SCANNING PROBE MICROSCOPE HAVING A DIRECTIONAL COUPLER AND A Z-DIRECTION DISTANCE ADJUSTING PIEZOELECTRIC ELEMENT

[75] Inventor: Masatoshi Yasutake, Tokyo, Japan

[73] Assignee: Seiko Instruments Inc., Tokyo, Japan

[21] Appl. No.: 57,767

[22] Filed: May 7, 1993

[30] Foreign Application Priority Data

May 8, 1992 [JP] Japan .................................. 4-116339

[51] Int. Cl.⁵ .............................................. H01J 3/14
[52] U.S. Cl. ................................. 250/234; 250/227.11
[58] Field of Search ................... 250/234, 216, 227.11, 250/306, 307; 73/104, 105, 78, 87; 318/640, 116, 118

[56] References Cited

U.S. PATENT DOCUMENTS 5,168,159  12/1992  Yagi ..................................... 250/307
5,237,859  8/1993  Elings et al. ........................ 250/306

Primary Examiner—David C. Nelms
Assistant Examiner—Que T. Le
Attorney, Agent, or Firm—Spensley Horn Jubas & Lubitz

[57] ABSTRACT

In a probe-scanning type of microscope, a cantilever arm carries a probe, a Z-direction distance adjusting piezoelectric element for adjusting the distance of the cantilever arm in a Z direction and the end portion of a fiber for directing a laser beam onto the back surface of the cantilever arm are secured to a three-dimensional scanner tube for scanning in X,Y and Z directions, whereby displacement of the cantilever arm is measured by observing interference of light.

6 Claims, 8 Drawing Sheets

I : LIGHT INTENSITY $\varphi$ : PHASE DIFFERENCE

SCANNING PROBE MICROSCOPE HAVING A DIRECTIONAL COUPLER AND A Z-DIRECTION DISTANCE ADJUSTING PIEZOELECTRIC ELEMENT

BACKGROUND OF THE INVENTION

This invention relates to a microscope such as an Atomic Force Microscope (AFM), a Magnetic Field Microscope (MFM), etc. and particularly to a microscope for measuring a large-size sample.

In a conventional AFM apparatus, an optical lever system is disclosed as a displacement detection system in the z-direction (the thickness direction of a sample) in a paper entitled "An atomic-resolution atomic-force microscope implemented using an optical lever" by S. Alexander, et al., published in the Journal of Applied Physics 65 (1), 164–167 (1988). Further, an optical wave interference system is also disclosed in "Atomic Force microscope-force mapping and profiling on a sub 100 Å scale" by Y. Martin, et al., Journal of Applied Physics 61 (10), 1987. In both systems, a force occurring between a sample surface and a probe having a sharp tip is converted to the displacement of a cantilever having the shape of a weak spring, the probe being secured to the tip of the cantilever.

In the first method, an opposite-side surface to the probe of the spring-shaped cantilever is mirror polished, a laser light is irradiated onto the mirror polished surface, and light reflected therefrom is detected by a bi-sectional photodiode. Thereafter, the difference in light amount detected by the two photodiode parts is detected as the displacement of the cantilever (spring), that is, an uneven status of the sample surface, and then converted to an electrical signal.

In the second method, the spring is vibrated at its resonant frequency, and its frequency and amplitude are monitored by an optical wave interference method. The frequency and amplitude of this vibration is varied due to a fine force acting between the sample and the probe and this variation is detected as an electrical signal (hereinafter referred to as "AC detection method").

The force acting between the sample and the probe is converted to a signal representing the displacement of the spring, and the converted electrical signal is input to a servo system and thus a z direction piezoelectric scanner at a sample stand side to thereby control the z-direction of the sample stand so that the force acting between the sample and the probe is constant. At this time, an in-plane scanning of the probe is carried out by the XY direction piezoelectric scanner in a fixed area of the sample, and through this operation a three-dimensional image of the sample surface is obtained.

At present, in the optical lever system, the sample surface is scanned with a force of about $10^{-9}$N acting between the sample and the probe by a direct-current detection method, and it has been widely used for AFM. On the other hand, the AC detection method has been exclusively used in the optical wave interference system, and it has been used as a spring displacement detection system for a magnetic force microscope.

Hitherto, in both the optical lever system and the optical wave interference system, the sample is mounted on the three-dimensional piezoelectric scanner (scanner tube), and the probe is relatively swept on the sample surface at high sped. In order to carry out a high-speed scanning, it is required to miniaturize the scanner and keep it highly rigid. Therefore, the construction that the sample is mounted on the three-dimensional scanner tube imposes restrictions on the size and weight of the sample. At present, the size and weight of a securable sample is about 2 cm square and about 1 g, respectively.

A second problem will occur in complex technologies with other observing means. In the optical lever system, a fixed positional relationship is required to be kept between a laser generator serving as a light source, a cantilever and a photodiode, and these elements cover most of the sample surface to be measured and observed. Therefore, it is difficult to install an optical lever system of an AFM apparatus into a revolver portion for exchanging an objective lens of an optical microscope.

In the optical wave interference system, an interferometer portion can be disposed far away and a detection portion can be also disposed far away from the sample because an optical fiber is used. Therefore, it is effectively used for composite with other apparatuses and remote detection. However, in order to stably obtain interference fringes, a stable He-Ne laser must be used, and thus the whole construction of the apparatus is required to be designed to be of large size.

SUMMARY OR THE INVENTION

A primary object of the present invention is to provide a solution to the above-described problems by providing an improved optical lever system for mapping a sample surface.

The above and other objects are achieved, according to the present invention, by the provision of a comprising a probe disposable adjacent a surface of a sample to be measured when the sample is disposed so that the surface extends generally in a plane having mutually perpendicular X and Y coordinates, in order to detect the dimension of the sample surface in a Z direction perpendicular to the plane;

a cantilever arm having a base end and a tip end and carrying the probe at the tip end, the cantilever arm having a spring property allowing the probe to be displaced by a distance corresponding to the dimension of the sample surface in the Z direction, the cantilever arm further having a front surface from which the probe projects and a back surface that faces away from the front surface;

a Z-direction distance adjusting piezoelectric element which can be stretched and contracted in the Z direction, the cantilever arm being supported at the base end by the piezoelectric element;

laser means for producing a light beam and a first photodiode;

a first directional coupler coupled to a first optical fiber having an end surface, the first directional coupler being arranged for directing the light beam produced by the laser means through the first optical fiber so that the light beam exits the first optical fiber via the end surface and impinges on the back surface of the cantilever arm, and for directing light reflected from the back surface of the cantilever arm and light reflected within the first optical fiber from the end surface of the first optical fiber to the first photodiode; and a three-dimensional scanner tube which supports the first optical fiber so that light exiting from the first optical fiber end surface impinges on the back surface of the cantilever arm, and which supports the Z-direction distance adjusting piezoelectric element, the three-dimensional scanner tube being deformable in the X, Y and Z directions to cause the probe to scan the sample surface.

As described above, a mechanism for scanning a sample surface is secured at a cantilever side to enable a scanning operation of a probe without moving a sample. Therefore, the size and weight of the sample can be increased. Further, light is irradiated onto the back surface of the cantilever through an optical fiber, so that the apparatus can be miniaturized and secured to another microscope, for example a revolver for securing an objective lens of a metal microscope.

DESCRIPTION OF THE PREFERRED EMBODIMENTS

An embodiment of this invention will be described with reference to the accompanying drawings.

Figure 1:
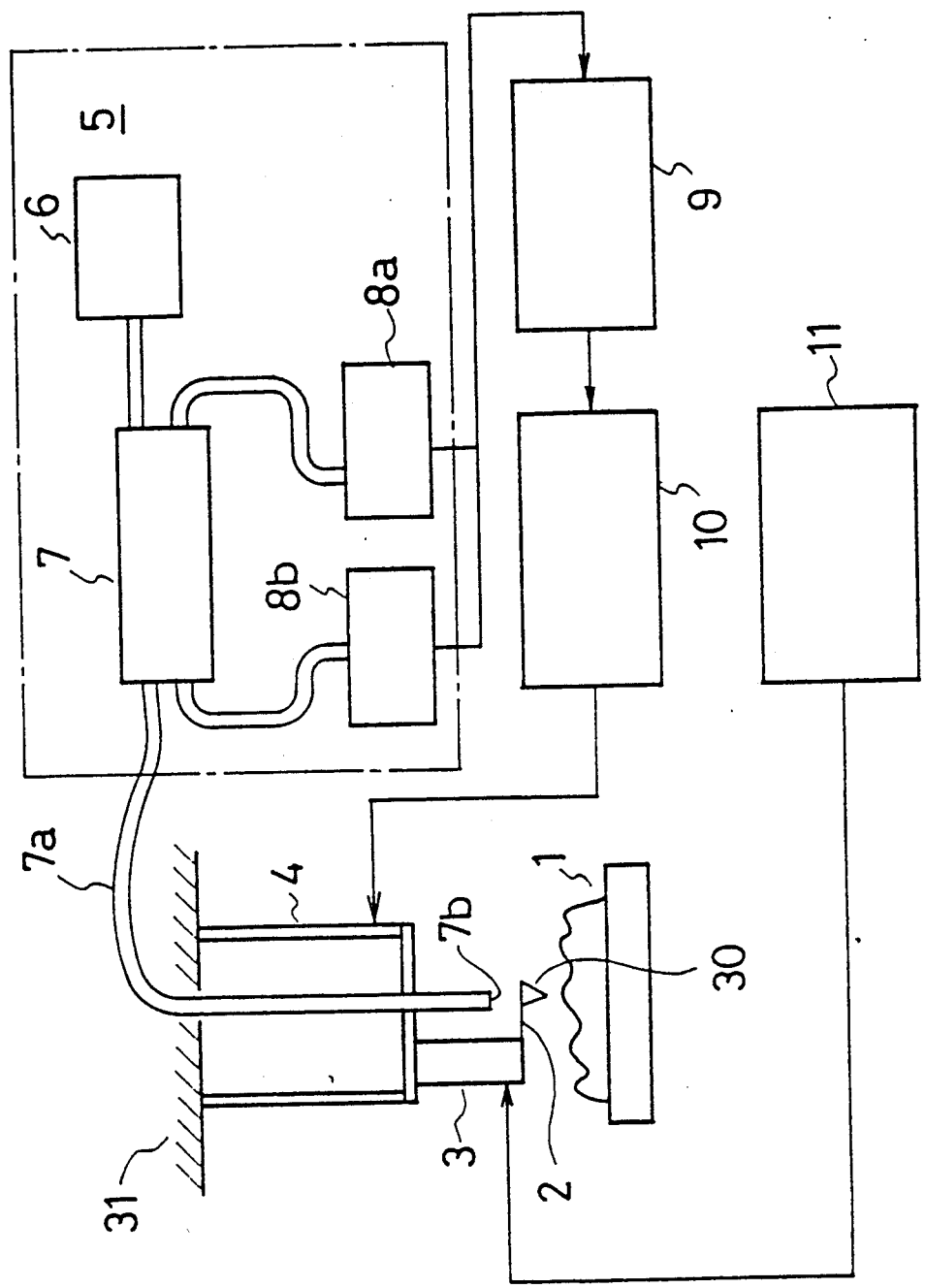
FIG. 1 is partly a cross-sectional view and partly a block diagram of an embodiment of the invention.

FIG. 1 is a block diagram and cross-sectional view of an apparatus using an optical fiber interferometer. A cantilever 2 is disposed above a sample 9. The cantilever 2 is designed in the form of a spring plate and a sharp needle-like probe 30 is provided at the tip of the cantilever 2. The tip of the probe 30 pushes on the surface of the sample 1 with a weak force of about $10^{-9}$N. A repulsive force is induced due to the inter-atomic force between the surface of the sample 1 and the tip of the probe 30. The cantilever 2 is displaced to an equilibrium position due to the balancing of these forces. The probe 30 serves to detect the physical height of the surface of the sample 1, and the cantilever 2 is displayed (sags) due to its spring property in accordance with the physical height. For example, a light beam from a directional coupler 7 is passed through a fiber 7a and irradiated through the end surface 7b of the optical fiber 7a to the back surface of the cantilever 2 to measure displacement of the cantilever 2 on the basis of the interference of the light beam.

In order to adjust the distance between the end surface 7b of the fiber 7a and the back surface of the cantilever 2 and vibrate the cantilever 2 in an AC detecting operation, the cantilever 2 is supported by a z-direction distance adjusting piezoelectric element 3. The z-direction distance adjusting piezoelectric element 3 and the end portion of the fiber 7a are secured to a three-dimensional scanner tube 4. The three-dimensional scanner tube 4 serves to allow the probe 30 to scan the surface of the sample 1 along a plane (X,Y) and at the same time moves the probe 30 upwardly and downwardly (in the z-direction) in accordance with the unevenness of the surface. That is, the stretching and contracting motion of the three-dimensional scanner tube 4 in the z-direction is controlled by a servo system 10 so that the displacement (sagging amount) of the cantilever 2 is constant. The three-dimensional scanner tube 4 is supported by a support plate 31 at the end thereof remote from element 3.

Figure 2:
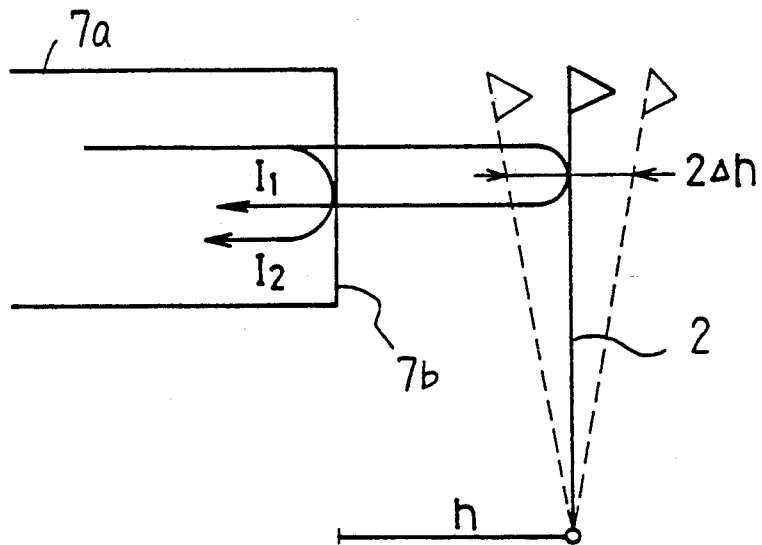
FIG. 2 is a cross-sectional pictorial view showing light reflected from the back surface of a cantilever and the end surface of a fiber.

Next, a displacement detection optical system 5 will be described. A semiconductor laser 6 is provided as a light source. A gas laser such as an He-Ne or the like is usable as the light source. If occasion demands, an isolator (not shown) may be provided at the emission side of the semiconductor laser 6 to prevent return light from entering the semiconductor laser 6. The light irradiated from the semiconductor laser 6 is guided into the directional coupler 7, passed through the fiber 7a whose end portion is secured to the three-dimensional scanner tube 4, irradiated to the cantilever 2 from the end surface 7b of the fiber 7a as shown in FIG. 2, and then reflected and returned to the fiber 7a again. The light reflected from the cantilever 2 is represented by $I_1$. On the other hand, light from the semiconductor laser 6 is reflected from the end surface 7b of the fiber 7a. The light reflected from the end surface 7b of the fiber 7a is represented in FIG. 2 by $I_2$.

The light $I_1$ reflected from the cantilever 2 and the light $I_2$ reflected from the end surface 7b go backward in the fiber 7a again, and reach the directional coupler 7. Here, interference fringes are generated from the two light components $I_1$ and $I_2$ on the surface of a first photodiode 8a which is coupled via a fiber to the directional coupler 7. The variation in light and darkness of the interference fringes corresponds to the displacement of the cantilever 2. On the other hand, a second photodiode 8b which is coupled via a fiber to the directional coupler 7 monitors variation in intensity of the light source of the semiconductor laser 6, and it is used to remove influence of the variation in intensity of the light source on the interference fringes as described above. The signals from the first and second photodiodes 8a and 8b are transmitted to a displacement detecting electric system 9 to subject the signals to amplification and calculation, and then output to Z-axis servo system 10. In the Z-axis servo system 10, a displacement set value of the cantilever 2 and the current displacement are compared and the difference therebetween is amplified. The amplified difference is applied to a Z-axis driving electrode (not shown) of the three-dimensional scanner tube 4 to control the cantilever 2 such that the displacement thereof is constant at all times. That is, the probe 30 is driven to scan the surface of the sample such that an inter-atomic force between the surface of the sample 1 and the tip of the probe 30 is constant, or, in other words, the three-dimensional scanner tube 4 is stretched and contracted in the z-direction in accordance with the unevenness of the surface of the sample.

Next, the operation principle of the displacement detecting optical system will be described. As shown in FIG. 2, interference fringes represented by the following equation are induced on the first photodiode 8a by the light component $I_2$ reflected from the end surface 7b of the fiber 7a and the light component $I_1$ reflected from the cantilever 2.

$$I = I_1 + I_2 + 2(I_1 \cdot I_2)^{\frac{1}{2}} \cos\Phi \tag{1}$$

$\Phi$: phase difference

Here, assuming that $I_1 = I_2 = I_0 \ldots (2)$, the light intensity on the first photodiode 8a is represented as follows:

$$I = 2I_0(1 + \cos\Phi) \tag{3}$$

Figure 3:
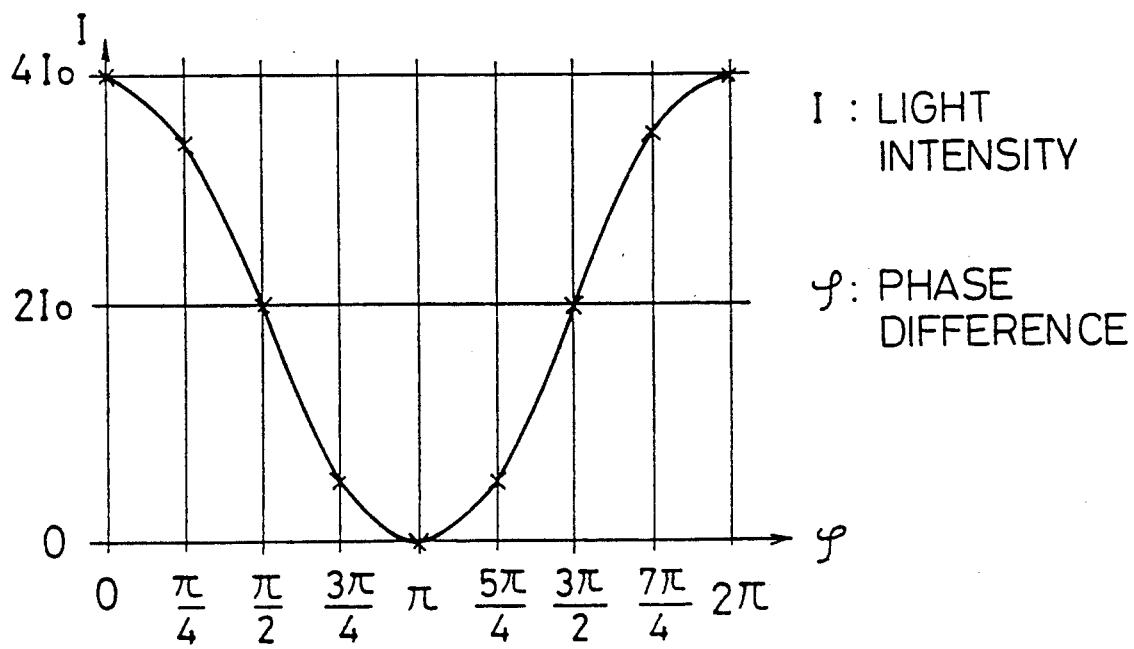
FIG. 3 is a graph showing the relationship between detected light intensity and light phase difference.

The equation (3) (the relationship between the phase difference and the intensity of interference fringes) is shown in FIG. 3. As is apparent from FIG. 3, in order to detect a fine displacement k of the cantilever 2, as shown in FIG. 3, it is required to set the phase difference to an area ($\pi/4 < \Phi < 3\pi/4$, or $5\pi/4 < \Phi < 7\pi/4$) where the interference fringes vary linearly. In order to satisfy this requirement, the distance h between the end surface 7b of the fiber and the back surface of the cantilever 2 may be set to a value represented by the following equations:

$$2\Phi = \pi/2 + 2m\pi \tag{4}$$

$$h = \lambda/8 + m\lambda/2 \tag{5}$$

Here, m represents an integer, and $\lambda$ presents the wavelength of the light.

In order to satisfy this condition, the z-direction distance adjusting piezoelectric element 3 as shown in FIG. 1 is provided. Actually, it is assumed that $h = 10$ $\mu m$ and $m \approx 31$ for $\lambda = 633$ nm. When the cantilever 2 is displaced by $\Delta h$ with the distance h satisfying the equation (5) at the center thereof, it is detected as a variation in intensity of interference fringes as represented by an equation (6):

$$\Delta h = 2I_0(1 + \sin\Delta\Phi)$$

$$\Delta\Phi = (4\pi\Delta h)/\lambda \tag{6}$$

For example, assuming that $\Delta h = 10$ nm, the variation in intensity is 18% on the basis of the equation (6). This variation in light amount is detected by the photodiode, and used as a displacement signal of the cantilever 2.

Figure 4:
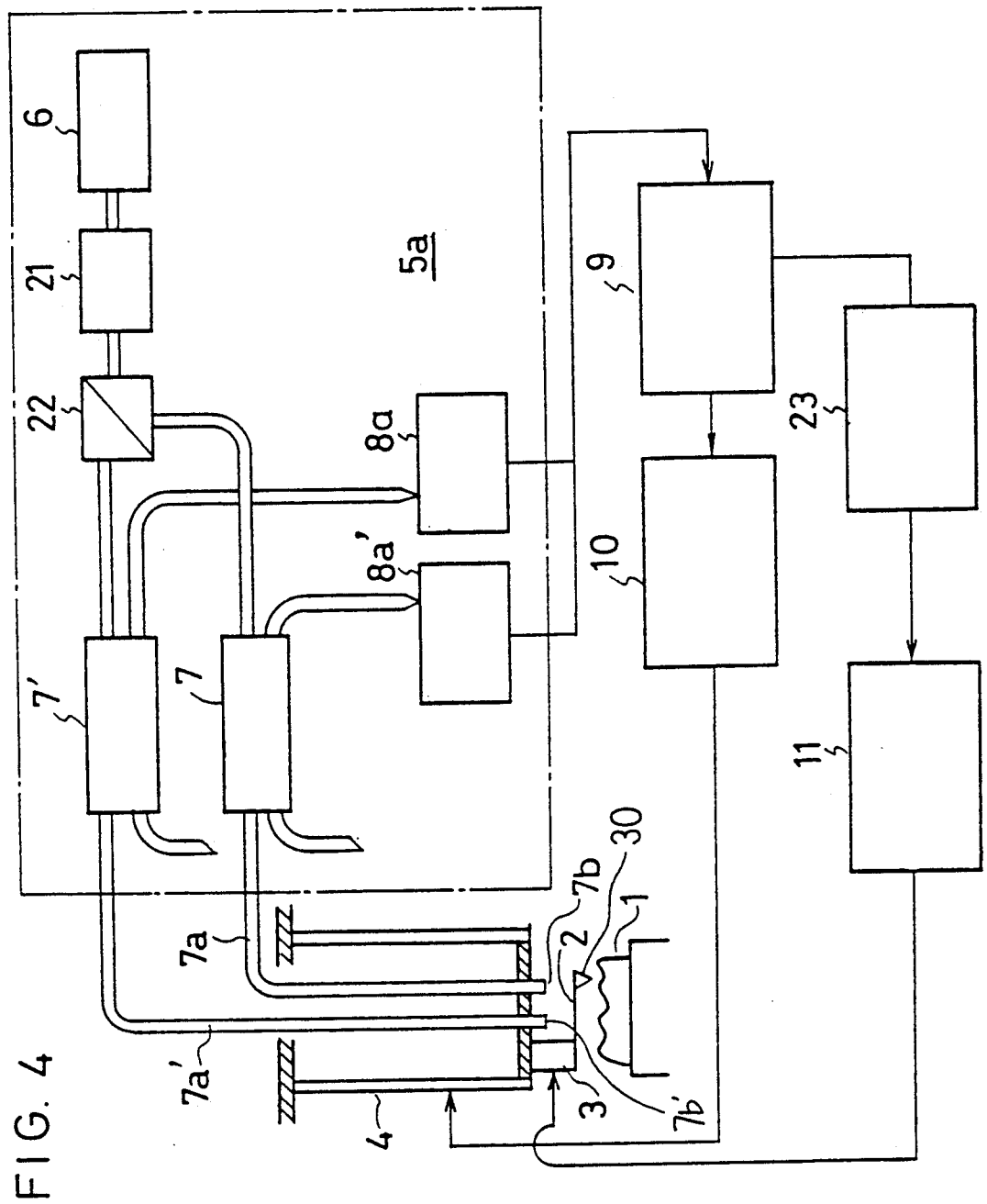
FIG. 4 is partly a cross-sectional view and partly a block diagram for another embodiment of this invention.

FIG. 4 shows another embodiment. The construction as shown in FIG. 1 has a weak resistance against variation in wavelength of the light source, fluctuation of the atmosphere, etc. in principle. On the other hand, in the construction as shown in FIG. 4, two pair of interferometers as shown in FIG. 1 are provided, and the variation factor as described above is reduced.

In the construction of this embodiment, a probe 30 is disposed above a sample 1 such that the tip of probe 30 confronts the sample 1, and a cantilever 2 is fixed to a modulating piezoelectric element 3 which is also used as a z-direction distance adjusting element. A three-dimensional scanner tube 4 supports the modulating piezoelectric element 3 and two fibers 7a and 7a' at the end portion thereof. A displacement detecting optical system 5a of this embodiment is equipped with a semiconductor laser 6 serving as a light source, and an isolator 21 which is disposed at the light emission side thereof to prevent return light from entering the semiconductor laser 6. A beam splitter 22 is provided at the emission side of the isolator 21. The beam splitter 22 serves to divide the laser beam and irradiate the divided laser beams to a pair of directional couplers 7, 7' respectively. Light beams from the directional couplers 7, 7' are passed through the respective fibers 7a, 7a' and irradiated to the back surface of the cantilever 2.

The light from the end surface 7b' of one of the fibers 7a' is irradiated to a support portion (base) of the back surface of the cantilever 2, and the light from the end surface 7b of the other fiber 7a is irradiated to the tip portion of the back surface of the cantilever 2.

The light reflected from the back surface of the cantilever 2 is passed through the respective directional couplers 7, 7' and then detected by respective first photodiodes 8a, 8a'. The light signals detected by the respective first photodiodes 8a, 8a' are transmitted to a displacement detecting electric system 9 and further transmitted as a displacement signal to a Z-axis servo system 10. The Z-axis servo system 10 controls the three-dimensional scanner tube 4 to be stretched and contracted in the z-direction so that the displacement (sag) of the cantilever 2 relative to the surface of sample 1 is constant.

Figure 5:
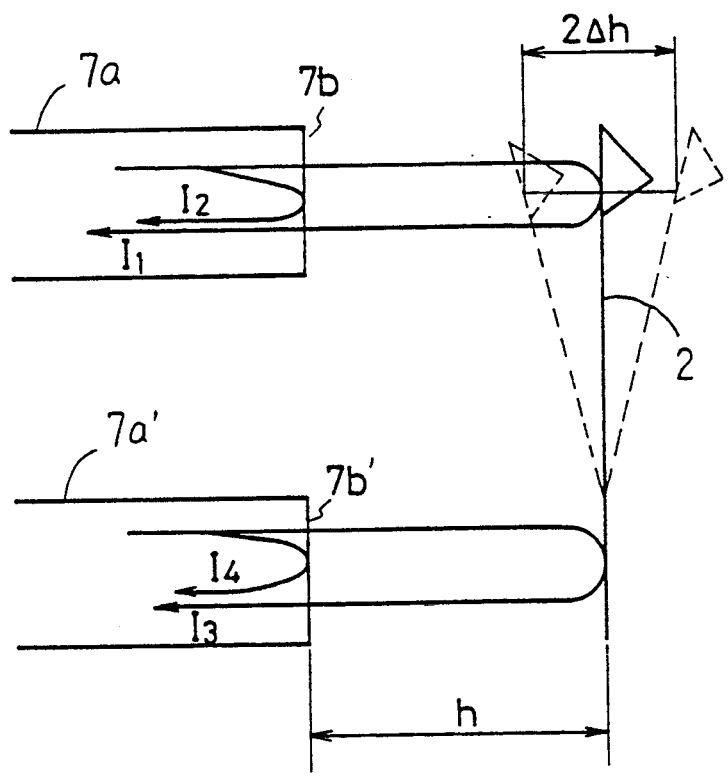
FIG. 5 is a cross-sectional view of light reflected from the back surface of an operation-type of a cantilever and the end surface of a fiber.

Next, the operation principle of the displacement detecting optical system 5a will be described. As shown in FIG. 5, light is irradiated from the end surface 7b of the fiber 7a to the tip portion of the cantilever 2 to obtain a detection signal, and light is also irradiated from the end surface 7b' of the other fiber 7a' to the base portion of the cantilever 2 to obtain a reference signal.

Assuming that light reflected from the tip portion of the back surface of the cantilever 2 is used as a signal light (s) and the light reflected from the base portion of the back surface of the cantilever 2 is used as a reference light (r), interference fringes on the respective first photodiodes 8a, 8a' are represented as follows:

$$I_s 2I_0(1 + \cos\Phi_s) \tag{7}$$

Here, it is assumed that $I_3 = I_4 = I_0$ (as described above).

$$I_r = 2I_0(1 + \cos\Phi_r) \tag{8}$$

Here, it is assumed that $I_1 = I_2 = I_0$. $I_3$ represents intensity of a reflected light from the base portion of the back surface of the cantilever 2, and $I_4$ represents intensity of a reflected light from the end surface 7b' of the fiber.

Here, fixing h under the condition of the equation (5) and representing the phase difference due to the optical difference h by $\Delta\Phi$ and representing the phase difference due to external disturbance by $\epsilon$ $$\Delta I_s = 2I_0]1 + \sin(\Delta\Phi + \epsilon) \tag{9}$$

$$\Delta I_r = 2I_0(1 + \sin\epsilon) \tag{10}$$

here, $\Delta\Phi = (4\pi\Delta h)/\lambda$

The signal light and the reference light are determined on the basis of the above equations.

Here, $\Delta I_s - \Delta I_r$ is calculated by the displacement detecting electric system 9 of this embodiment. Since $\Delta\Phi > \epsilon$ and $\Delta\Phi$ is sufficiently small in practical use, the above value may be replaced by the following value:

$$\Delta I_s - \Delta I_r = \sin\Delta\Phi, \Delta\Phi = (4\pi\Delta h)/\lambda \tag{11}$$

From the equation (11), a signal corresponding to the displacement of the cantilever 2 is obtained. In the construction of this embodiment, not only the external disturbance, but also the variation of wavelength of the light source, time-drift of the set distance h between the cantilever 2 and the end surface 7b of the fiber 7a can be removed, and the displacement detection signal can be stably obtained.

In order to positively remove the time drift of the set distance h, in addition to the z servo system 10, the apparatus of FIG. 4 may be provided with a servo system 23 for cantilever distance control as another loop. In this case, a power source 11 for the piezoelectric element is controlled such that the intensity of the reference light $I_r$ is constant. The cantilever distance controlling servo system 23 is controlled with a longer time constant than the Z-axis servo system 10.

The above description, relates to a method for detecting in a direct-current mode the displacement of the cantilever 2 disposed near to the sample, which has been well used for AFM. Next, the measurement method and the construction thereof for performing a detection in an alternating mode, which has been well used for MFM, will be described with reference to FIG. 6.

The apparatus of this embodiment is equipped with an oscillator 24. In a state where the cantilever 2 is disposed away from the surface of the sample 1 at a spacing interval of about 10 to 100 nm, an alternating voltage of frequency ω is applied through the power source 11 for the piezoelectric element to the z-direction adjusting piezoelectric element 3 power source 11 being driven by the oscillator 24. The cantilever 2 is sharply resonated at a frequency near to its resonant frequency $\omega_0$. When in this state the cantilever 2 and the surface of the sample 1 are made to approach one another to reduce the distance therebetween below 10 nm, the resonance frequency and the amplitude of the resonance are varied. Here, representing a differential field of a force in the z-direction acting between the surface of the sample 1 and the tip of the probe 30 by F', the spring constant of the cantilever 2 by k and the Q-value of the resonance by Q, the deviation (variation) of the frequency and the variation of amplitude are represented as follows:

$$\Delta\omega = F'\omega_o/(2k) \quad (12)$$

$$\Delta A = 2QF'\omega_0 \Delta h/[3(\sqrt{3})k] \quad (13)$$

These variations are detected as the interference of the optical wave irradiated from the end surface 7b of the fiber. Assuming the average distance h between the fiber end surface 7b and the back surface of the cantilever 2 to be fixed to a value defined by equation (5), the interference fringes in a state where no differential field F' is applied are represented by the following equations:

$$\Delta I(t) = 2I_0[1 + \sin\Delta\Phi(t)]$$

$$\Delta\Phi(t) = [2\pi \cdot 2\Delta h(t)]/\lambda$$

$$2\Delta h(t) = 2\Delta h \sin\omega_0 t \quad (14)$$

Figure 6:
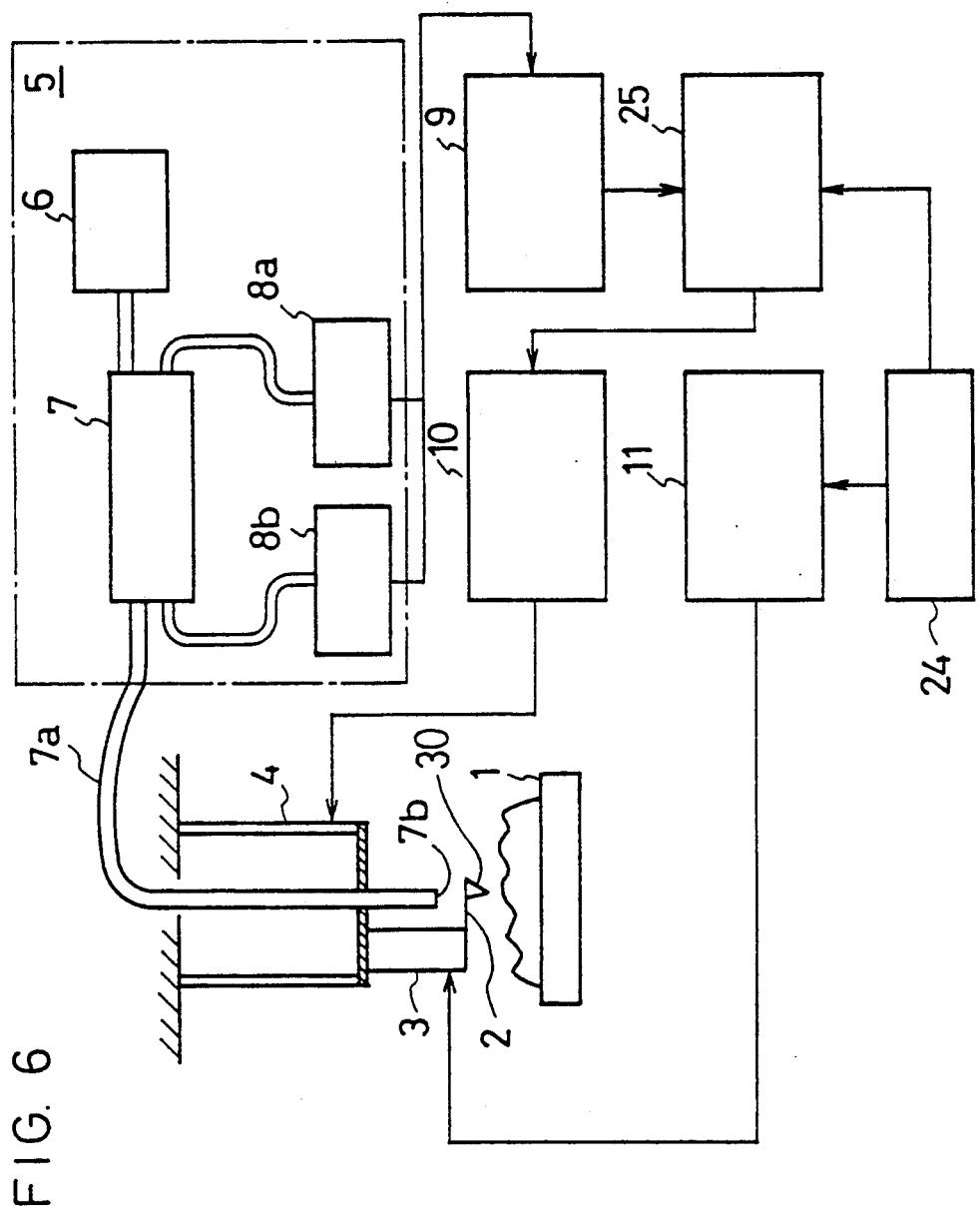
FIG. 6 is partly a cross-sectional view and partly a block diagram of another embodiment of this invention.

Accordingly, if a phase detection is carried out by a lock-in amplifier 25 as shown in FIG. 6, the deviation (variation) in frequency or the variation in amplitude which are represented by the equations (12) and (13) can be monitored. The Z-axis of the three-dimensional scanner tube can be stretched and contracted through the Z-axis servo system 10. This AC detection method has a high force detection sensitivity of about $10^{-13}$N, and is used for a detection system for an MFM.

Figure 7:
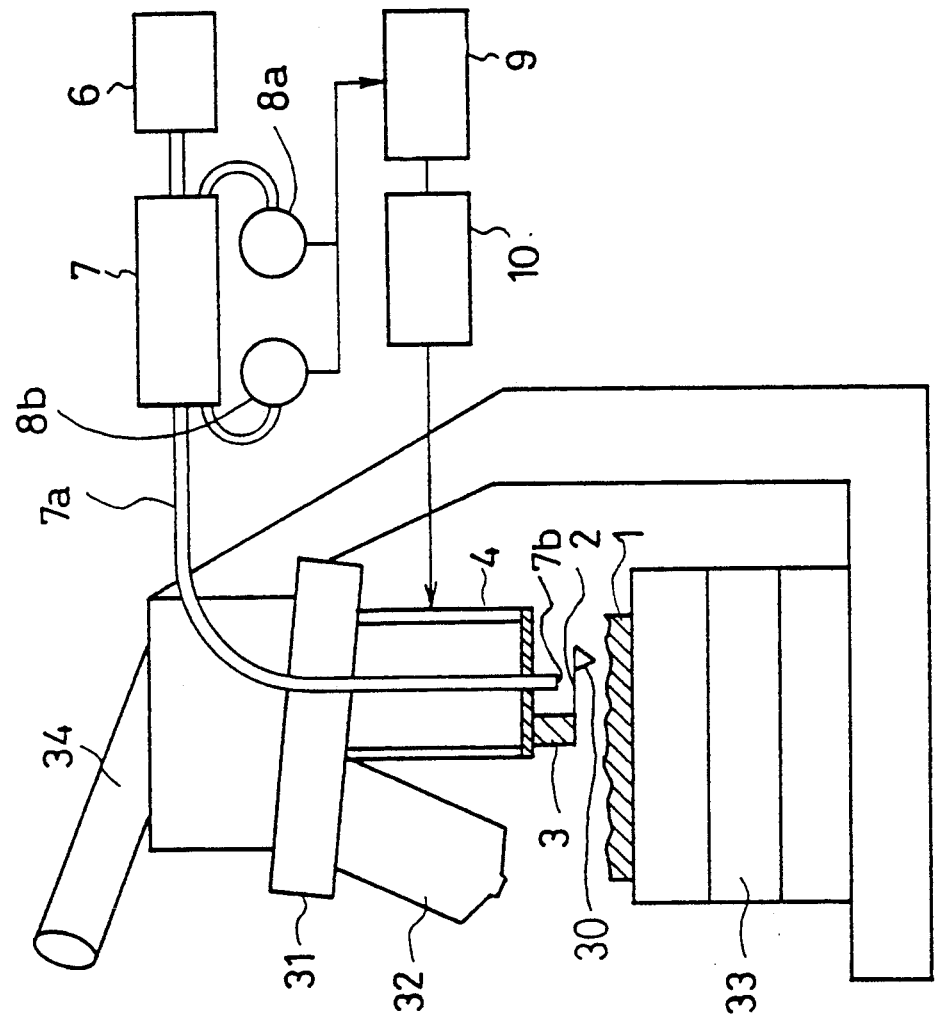
FIG. 7 is partly a cross-sectional view of an embodiment of the invention applied to a metal microscope.

Next, a case where the interferometer as shown in FIG. 1 or FIG. 4 is installed in an apparatus will be described. FIG. 7 shows a case where the three-dimensional scanner tube assembly as shown in FIG. 1 is installed in a revolver portion, or turret, 31 for mounting an objective lens of an optical microscope (metal microscope). The three-dimensional scanner tube assembly includes the three-dimensional scanner tube 4, the z-direction distance adjusting piezoelectric element 3, the probe 30, the cantilever 2 and the end portion of the fiber 7a. In this construction, the surface of a large sample 1 mounted on a XYZ stage 33 is observed through an objective lens 32 by an eyepiece 34 to locate a desired point on sample 1, which point is moved to substantially the center portion of a visual field. Subsequently, the revolver 31 is rotated to locate the three-dimensional scanner tube assembly on the surface of the sample and carry out a measurement of AFM. As described above, the microscope and the AMF can be compactly integrated, and thus the determination of an observation area for the AMF can be facilitated. In addition, a large-size sample 1 and a heavy-weight sample 1 can be observed and measured.

Figure 8:
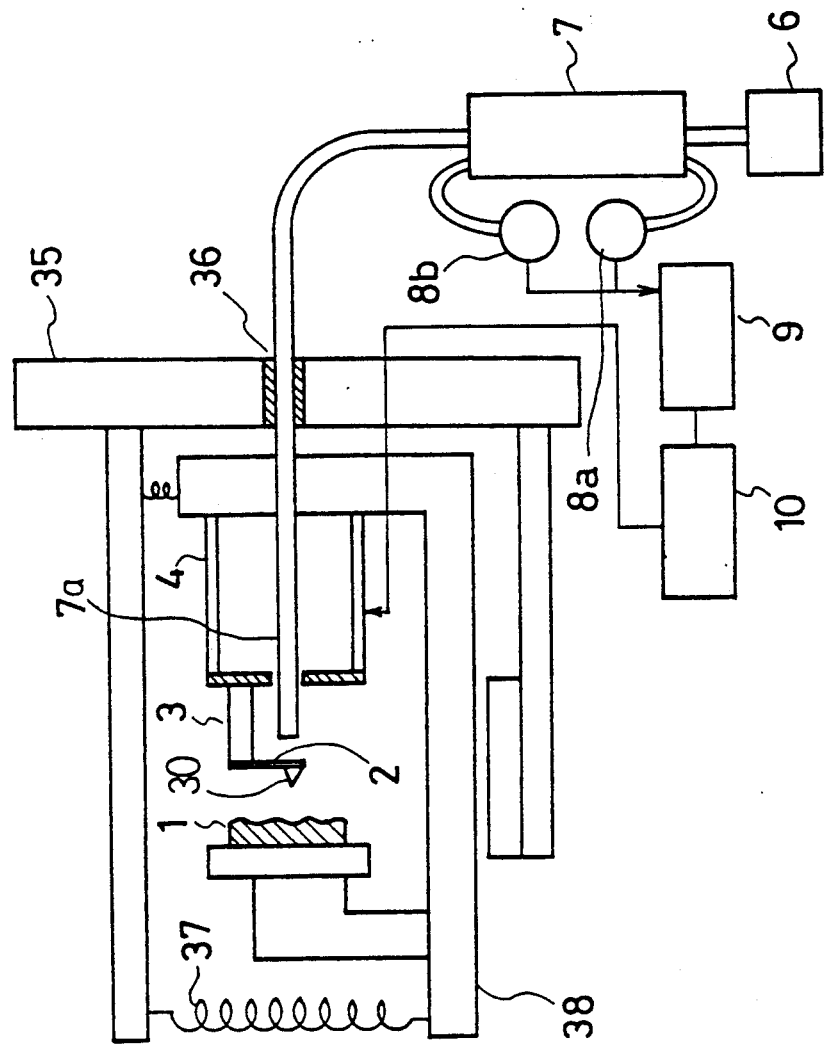
FIG. 8 is partly a cross-sectional view of an embodiment of the invention applied in an ultra-high vacuum.

FIG. 8 shows a case where the interferometer is installed in an ultra-high vacuum AFM. A vacuum flange 35 is secured to a vacuum chamber (not shown). That is, the left side of FIG. 8 is kept in an ultra-high vacuum. A passageway for displacement detecting light includes the fiber 7a, and thus a passage for the light is easily formed in the vacuum flange 35. Therefore, the semiconductor laser 6, the directional coupler 7, the first and second photodiodes 8a and 8b and the electric control system, serving as a detection portion in combination, can be disposed outside the vacuum chamber. The three-dimensional scanner tube assembly 4, 3, 30, 2 and 7a and the sample 1 are disposed in vacuum. These elements are supported by a stand 38 whose vibration is arrested by a vibration-arresting mechanism 37. When a quartz fiber cable is used as the fiber 7a, it can withstand damage when subjected to high-temperature baking.

Figure 9:
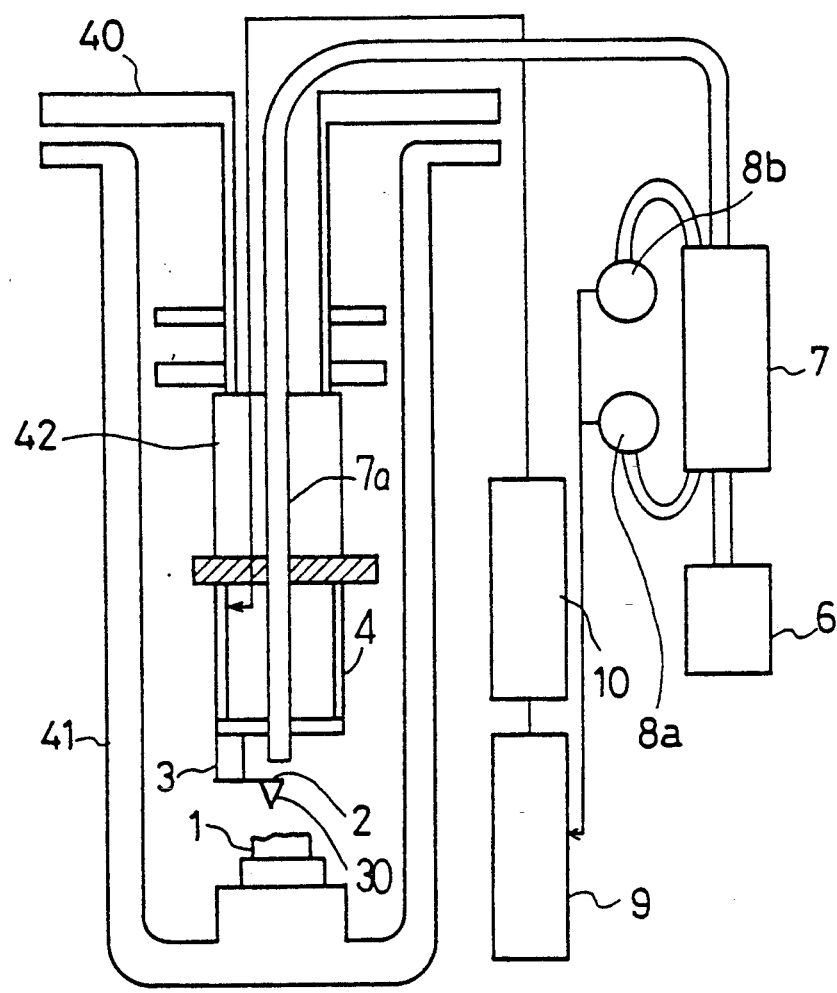
FIG. 9 is partly a cross-sectional view of an embodiment of the invention applied in a low-temperature tank.

FIG. 9 shows a case where the interferometer is installed in a low-temperature AFM. A cryostat flange 40 is secured to a cryostat chamber 41. That is, the region enclosed by flange 40 and chamber 41 is kept at a low temperature. Since the passageway for displacement detecting light comprises the fiber 7a, it can be easily provided in the cryostat flange 40, and the semiconductor laser 6, the directional coupler 7, the first and second photodiodes 8a and 8b and the electric control system which serve as the detection portion can be disposed at the outside. The three-dimensional scanner tube assembly 4, 3, 30, 2 and 7a and the sample 1 are kept at a low temperature. The three-dimensional scanner tube 4 is secured to a Z-axis coarse-moving mechanism 42.

In a microscope of this invention, since a directional coupler of optical fibers is used for the optical wave interference displacement detecting system, the system is compact. In addition, since the system is designed as a difference type (a pair of optical wave interference displacement detecting systems are used), the system has high resistance against variation of wavelength of the light source and external disturbances.

Further, since the probe scanning system and the probe system for detecting the displacement of the cantilever are integrated at the cantilever side, a large-size sample or a heavy-weight sample whose measurement has been conventionally difficult can be measured.

Still further, since the probe scanning system and the probe system for detecting the displacement of the cantilever are designed so as to be compact and integrated, these systems can be installed in the revolver for securing an objective lens of a metal microscope. Therefore, the sample can be visually observed by the metal microscope, and the visually-observed sample surface can be easily and finely measured by the AFM or MFM. In addition, since the probe scanning system and the cantilever-displacement detecting probe system are designed so as to be integrated and compact, these systems can be disposed in an ultra-high vacuum chamber or in a low-temperature cryostat, so that the sample can be observed by an ultra-high vacuum or low temperature AFM or MFM.

This application relates to subject matter disclosed in Japanese Application number 4-116339, filed on May 8, 1992, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A microscope comprising:
   a probe disposable adjacent a surface of a sample to be measured when the sample is disposed so that the surface extends generally in a plane having mutually perpendicular X and Y coordinates, in order to detect the dimension of the sample surface in a Z direction perpendicular to the plane;
   a cantilever arm having a base end and a tip end and carrying said probe at said tip end, said cantilever arm having a spring property allowing said probe to be displaced by a distance corresponding to the dimension of the sample surface in the Z direction, said cantilever arm further having a front surface from which said probe projects and a back surface that faces away from said front surface;
   a Z-direction distance adjusting piezoelectric element which can be stretched and contracted in the Z direction, said cantilever arm being supported at said base end by said piezoelectric element;
   laser means for producing a light beam and a first photodiode;
   a first directional coupler coupled to a first optical fiber having an end surface, said first directional coupler being arranged for directing the light beam produced by said laser means through said first optical fiber so that the light beam exits said first optical fiber via said end surface and impinges on said back surface of said cantilever arm, and for directing light reflected from said back surface of said cantilever arm and light reflected within said first optical fiber from said end surface of said first optical fiber to said first photodiode; and
   a three-dimensional scanner tube which supports said first optical fiber so that light exiting from said first optical fiber end surface impinges on said back surface of said cantilever arm, and which supports said Z-direction distance adjusting piezoelectric element, said three-dimensional scanner tube being deformable in the X, Y and Z directions to cause said probe to scan the sample surface.

2. A microscope according to claim 1 wherein said three-dimensional scanner tube supports said first optical fiber so that light exiting from said first optical fiber end surface impinges on said back surface of said cantilever arm in the vicinity of said tip end of said cantilever arm.

3. A microscope according to claim 2 further comprising:
   a second photodiode;
   a second directional coupler including a second optical fiber having an end surface, said second directional coupler being arranged for directing light through said second optical fiber so that the light exits said second optical fiber via said end surface of said second optical fiber and impinges on said back surface of said cantilever arm in the vicinity of said base end of said cantilever arm, and for directing light reflected from said back surface of said cantilever arm and light reflected within said second optical fiber from said end surface of said second optical fiber to said second photodiode; and
   a beam-splitter disposed for dividing the light from said laser means into first and second components and for supplying the first component to said first directional coupler and the second component to said second directional coupler.

4. A microscope for observing a sample surface, comprising:
   a probe disposable adjacent the sample surface when the sample is disposed so that the surface extends generally in a plane having mutually perpendicular X and Y coordinates, in order to detect the dimension of the sample surface in a Z direction perpendicular to the plane;
   a cantilever arm having a base end and a tip end and carrying said probe at said tip end, said cantilever arm having a spring property allowing said probe to be displaced by a distance corresponding to the dimension of the sample surface in the Z direction, said cantilever arm further having a front surface from which said probe projects and a back surface that faces away from said front surface;
   a Z-direction distance adjusting piezoelectric element which can be stretched and contracted in the Z direction, said cantilever arm being supported at said base end by said piezoelectric element;
   a light source and a photodiode;
   a directional coupler having first and second ends coupled to first, second and third optical fibers, said first and third optical fibers being coupled to said directional coupler at said first end, said second optical fiber being coupled to said directional coupler at said second end and said second optical fiber having an output surface remote from said second end of said directional coupler, said directional coupler being coupled to said light source via said first optical fiber for directing light produced by said light source through said second optical fiber so that the light exits said second optical fiber via said output surface and impinges on said back surface of said cantilever arm, and for directing light reflected from said back surface of said cantilever arm and light reflected within said first optical fiber from said output surface of said second optical fiber to said photodiode via said third optical fiber; and a three-dimensional scanner tube which supports said second optical fiber so that light exiting from said second optical fiber output surface impinges on said back surface of said cantilever arm, and which supports said Z-direction distance adjusting piezoelectric element, said three-dimensional scanner tube being deformable in the X, Y and Z directions to cause said probe to scan the sample surface.

5. A microscope according to claim 4 wherein said second optical fiber is supported by said three-dimensional scanner tube so that the distance, h, between said output surface of said second optical fiber and said back surface of said cantilever arm is:

$$h = \lambda/8 + m\lambda/2,$$

where m is an integer, and $\lambda$ is the wavelength of the light produced by said light source.

6. A microscope according to claim 4 further comprising a revolver member for supporting an optical objective lens, and wherein said three-dimensional scanner tube, said Z-direction distance adjusting piezoelectric element, said cantilever arm, and said second optical fiber are supported by said revolver member.

* * * * *